United States Patent
Manginell et al.

(10) Patent No.: US 7,168,298 B1
(45) Date of Patent: *Jan. 30, 2007

(54) MASS-SENSITIVE CHEMICAL PRECONCENTRATOR

(75) Inventors: Ronald P. Manginell, Albuquerque, NM (US); Douglas R. Adkins, Albuquerque, NM (US); Patrick R. Lewis, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 118 days.

This patent is subject to a terminal disclaimer.

(21) Appl. No.: 10/903,329

(22) Filed: Jul. 29, 2004

Related U.S. Application Data

(63) Continuation-in-part of application No. 10/436,596, filed on May 12, 2003, now Pat. No. 6,823,720, and a continuation-in-part of application No. 10/436,597, filed on May 12, 2003, now Pat. No. 6,820,469.

(51) Int. Cl.
*G01N 11/10* (2006.01)
*G01N 30/00* (2006.01)
*G01N 30/12* (2006.01)

(52) U.S. Cl. ............... 73/54.25; 73/24.06; 73/579; 96/102; 96/108

(58) Field of Classification Search ........... 73/864.17, 73/54.25, 24.06, 54.41, 579, 19.01, 19.12, 73/31.07, 24.01, 590, 24.04, 335.02, 29.01, 73/864.71, 863.11, 863.24, 864.14, 23.41, 73/25.03; 95/90, 116, 148; 422/101, 102; 96/108, 147

See application file for complete search history.

(56) References Cited

U.S. PATENT DOCUMENTS

| | | | | | |
|---|---|---|---|---|---|
| 4,793,182 | A | * | 12/1988 | Djorup | 73/335.02 |
| 5,795,993 | A | * | 8/1998 | Pfeifer et al. | 73/24.01 |
| 5,836,203 | A | * | 11/1998 | Martin et al. | 73/579 |
| 6,125,687 | A | * | 10/2000 | McClelland et al. | 73/19.01 |
| 6,171,378 | B1 | * | 1/2001 | Manginell et al. | 96/143 |
| 6,527,835 | B1 | * | 3/2003 | Manginell et al. | 96/102 |
| 6,688,158 | B2 | * | 2/2004 | Cunningham et al. | 73/24.06 |
| 6,820,469 | B1 | * | 11/2004 | Adkins et al. | 73/54.25 |
| 6,851,297 | B2 | * | 2/2005 | Cunningham et al. | 73/24.06 |
| 7,118,712 | B1 | * | 10/2006 | Manginell et al. | 422/101 |
| 2006/0032290 | A1 | * | 2/2006 | Liu | 73/29.02 |

OTHER PUBLICATIONS

Adkins, Method for Chemical Sensing Using a Microfabricated Teeter-Totter Resonator, U.S. Appl. No. 10/436,596.

(Continued)

*Primary Examiner*—Hezron Williams
*Assistant Examiner*—Jacques Saint-Surin
(74) *Attorney, Agent, or Firm*—Kevin W. Bieg

(57) ABSTRACT

A microfabricated mass-sensitive chemical preconcentrator actively measures the mass of a sample on an acoustic microbalance during the collection process. The microbalance comprises a chemically sensitive interface for collecting the sample thereon and an acoustic-based physical transducer that provides an electrical output that is proportional to the mass of the collected sample. The acoustic microbalance preferably comprises a pivot plate resonator. A resistive heating element can be disposed on the chemically sensitive interface to rapidly heat and release the collected sample for further analysis. Therefore, the mass-sensitive chemical preconcentrator can optimize the sample collection time prior to release to enable the rapid and accurate analysis of analytes by a microanalytical system.

17 Claims, 8 Drawing Sheets

OTHER PUBLICATIONS

Adkins, Microfabricated Teeter-Totter Resonator, U.S. Appl. No. 10/436,597.

Greg Frye-Mason, Hand-Held Miniature Chemical Analysis System (μChemLab) for Detection of Trace Concentrations of Gas Phase Analytes, Proc, Micro Total Analysis Systems, 2000, SAND2000-1480A.

Greg Frye-Mason, Expanding the Capabilities and Applications of Gas Phase Miniature Chemical Analysis Systems (μChemLab), Proc. Micro Total Analysis Systems, 2001, SAND2001-3230A.

Martin, Gas Sensing with Acoustic Devices, Sensors and Actuators, B (b) (2) 1993:123, SAND96-2937C.

Adkins, Advanced Detectors for Chemical Weapon Detection, 2nd Joint Conf. On Point Detection for Chemical and Biological Defense, Mar. 1-5, 2004.

Martin, Flexural plate wave resonator excited with Lorentz forces, Journal of Applied Physics, 83, May 1, 1998, p. 4589-4601.

Grate, Acoustic Wave Microsensor Arrays for Vapor Sensing, Chem. Rev. 2000, 100, 2627-2648.

* cited by examiner

MASS-SENSITIVE CHEMICAL PRECONCENTRATOR

CROSS-REFERENCE TO RELATED APPLICATION

This application is a continuation-in-part of application Ser. No. 10/436,596, filed May 12, 2003 now U.S. Pat. No. 6,823,720, and a continuation-in-part of application Ser. No. 10/436,597, filed May 12, 2003 now U.S. Pat. No. 6,820,469, which are incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to microanalytical systems and, more particularly, to a microfabricated chemical preconcentrator that can actively measure the mass of a sample while it is being collected and then rapidly heat and desorb the collected sample to enable more rapid and accurate analysis of the sample by a microanalytical system.

BACKGROUND OF THE INVENTION

Portable, handheld microanalytical systems, which have been termed "chemical laboratories on a chip," are being developed to enable the rapid and sensitive detection of particular chemicals, including pollutants, high explosives, and chemical and biological warfare agents. These microanalytical systems should provide a high chemical selectivity, to discriminate against potential background interferents, and the ability to perform the chemical analysis on a short time scale with high sensitivity. In addition, low electrical power consumption is needed for prolonged field use. See G. C. Frye-Mason et al., *Proc. Micro Total Analysis Systems* 2000, Kluwer Academic Publisher, Dordrecht, The Netherlands, pp. 229–232, (2000) and G. C. Frye-Mason et al., *Proc. Micro Total Analysis Systems* 2001, Kluwer Academic Publisher, Dordrecht, The Netherlands, pp. 658–660, (2001).

In almost any chemical analysis system, there are three important stages: sample collection, sample separation, and sample identification. Current gas-phase microanalytical systems typically comprise a gas chromatography column to separate the chemical species, or analytes, in a gas sample and a detector to identify the separated species. Such microanalytical systems can also include a chemical preconcentrator for sample collection. The chemical preconcentrator serves the important function of collecting and concentrating the chemical analytes on a sorptive material at the inlet of the microanalytical system. The chemical preconcentrator can deliver an extremely sharp sample plug to the downstream gas chromatograph by taking advantage of the rapid, efficient heating of the sorbed analytes with a low-heat capacity, low-loss microhotplate. The very narrow temporal plug improves separations, and therefore the signal-to-noise ratio and sensitivity to the particular chemical species of interest. In particular, selective analyte preconcentration is an essential step for early-warning, trace chemical detection in real-world, high-consequence environments where a high background of potentially interfering compounds exists.

Previous microfabricated chemical preconcentrators have typically used a heated planar membrane suspended from a substrate as the microhotplate, wherein the sorptive material is disposed as a layer on a surface of the membrane to sorb the chemical species from a gas stream. The sorptive material thereby collects and concentrates the sample, and then the heated membrane thermally desorbs the sample in a short pulse for subsequent separation. See U.S. Pat. No. 6,171,378 to Manginell et al., which is incorporated herein by reference. Typically, samples are collected by the preconcentrator for a fixed period of time (e.g., 2 minutes) before they are released for analyte separation and identification. Collecting for a fixed time period is a fundamental shortcoming of the chemical analysis process. When concentrations of potential toxins are high, precious time is wasted collecting excess sample material. Furthermore, this excess material will often saturate the preconcentrator and overwhelm a detector, necessitating cleaning before further analysis can resume. Conversely, when target analyte concentrations in the sample stream are low, insufficient analyte may be collected for detection or proper identification.

To avoid these problems, the present invention is directed to a mass-sensitive chemical preconcentrator that actively measures the mass of the sample on a microbalance during the collection process. The entire microbalance can then be rapidly heated to release the sample for further analysis. Therefore, the mass-sensitive chemical preconcentrator can optimize the sample collection time prior to release to enable the rapid and accurate analysis of analytes by the microanalytical system.

SUMMARY OF THE INVENTION

The present invention is directed to a microfabricated mass-sensitive chemical preconcentrator for collecting and releasing a chemical sample, comprising an acoustic microbalance, comprising a chemically sensitive interface for collecting the sample thereon and an acoustic-based physical transducer that provides an electrical output that is proportional to the mass of the collected sample, and a resistive heating element disposed on the chemically sensitive interface to heat and release the collected sample from the chemically sensitive interface. The acoustic microbalance can comprise a surface acoustic wave device or a resonant microbalance.

Preferably, the mass-sensitive chemical preconcentrator comprises a pivot plate resonator, comprising a frame, a paddle having a first surface and a second surface for collection of the sample thereon, the paddle further having a first end and a second end, wherein the paddle is pivotably anchored to the frame by pivot arms at each end of the paddle and wherein the pivot arms define an axis of rotation of the paddle, a current conductor line disposed on a surface of the paddle that is displaced from the axis of rotation of the paddle, means for applying a static magnetic field aligned substantially in-plane with the paddle and substantially perpendicular to the current conductor line and the axis of rotation, and means for energizing the current conductor line with an alternating electrical current to excite an oscillatory motion of the paddle about the axis of rotation; a resistive heating element disposed on a surface of the paddle; and means for energizing the resistive heating element to thermally release the collected sample from the paddle.

The mass-sensitive chemical preconcentrator allows sample collection time to be adjusted dynamically to best suit the ambient concentration of the target analyte. For high target analyte concentrations, rapid collection and desorption can be performed. For low target analyte concentrations, slower analysis may be acceptable. The mass-sensitive chemical preconcentrator combines selective preconcentration with sample measurement functions in a single microscale platform, reducing analysis times up to an order of magnitude when the danger of toxicity is the greatest, and extending the dynamic range of microanalytical systems by placing the desorbed chemical concentration in the linear range of a downstream detector. In cases where rapid time response is necessary, the mass-sensitive chemical preconcentrator can provide an early indication of a chemical's presence and serve as a front-end trigger to initiate further analysis. Furthermore, the mass-sensitive chemical preconcentrator can extend the dynamic range of a microanalytical system, enabling rapid and accurate detection of chemical compounds in a highly integrated and low cost platform. Arrays of mass-sensitive chemical preconcentrators can be used to provide selective preconcentration of multiple analytes. Since all silicon processing is used in the fabrication of the mass-sensitive chemical preconcentrator, it can be monolithic integrated with drive and sense electronics.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
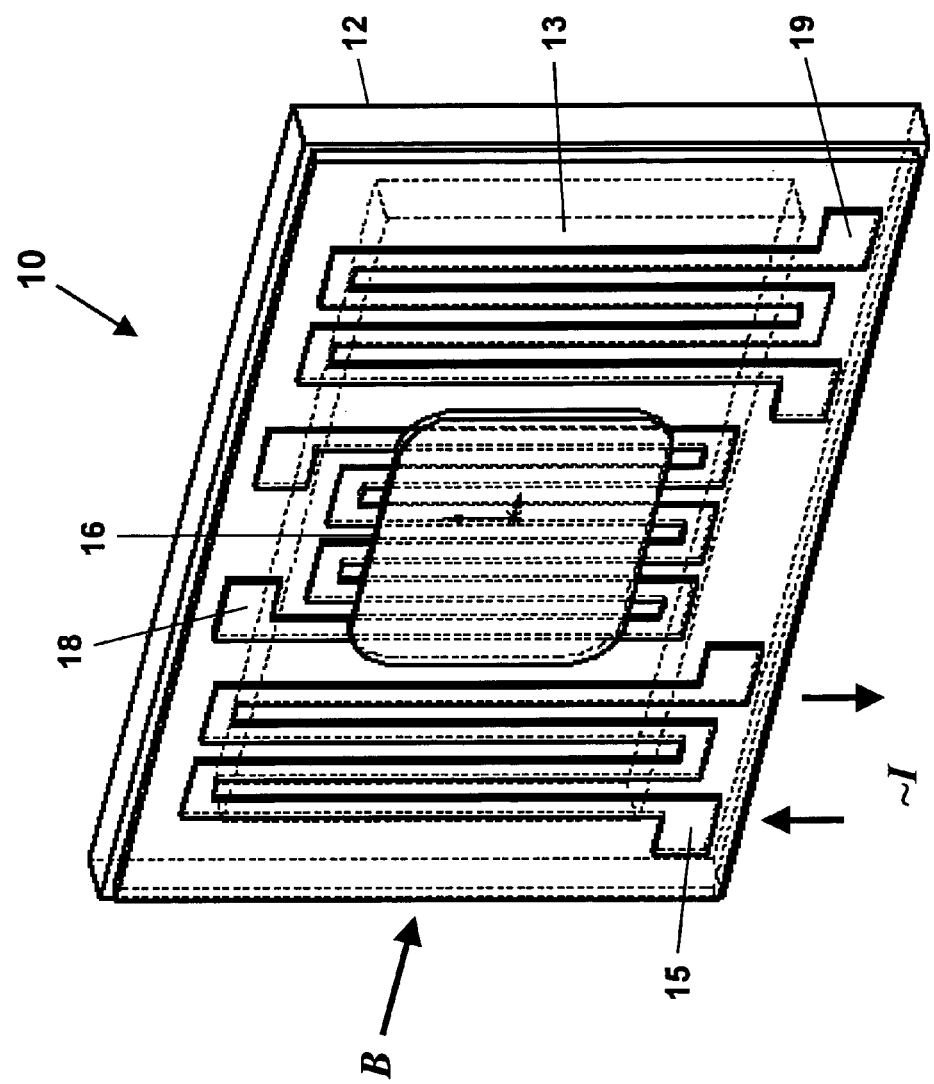
FIG. 1 shows a schematic illustration of a microfabricated mass-sensitive chemical preconcentrator that uses a flexural plate wave (FPW) resonator to actively measure the mass of a sample while it is being collected.

The capability to weigh a sample as it accumulates is made possible by the recent development of microfabricated acoustic devices. These acoustic devices have a number of applications, including frequency filtering, oscillator control, signal processing, and as mass and load sensors. When configured as a microbalance, these acoustic devices can be used as gas and vapor chemical sensors. When used as chemical sensors, the acoustic microbalance combines a chemically sensitive interface, which sorbs chemical species (i.e., analytes) from the environment, with an acoustic-based physical transducer, that provides an electrical output proportional to the amount of sorbed species. In particular, an acoustic microbalance relies on detecting the change in the acoustic behavior of the device (i.e., change in a mechanical wave propagation or structural vibration) due to the sorbed sample. Commonly used acoustic microbalances for chemical sensing include surface acoustic wave (SAW) devices and resonant microbalances. Resonant microbalances include, but are not limited to, the flexural plate wave (FPW) resonator, vibrating cantilever, resonating beam, and pivot plate resonator (PPR, also referred to as the teeter-totter resonator). See S. J. Martin et al., "Gas Sensing with Acoustic Devices," *Proc. IEEE Ultrasonics Symposium*, 423 (1996) and D. R. Adkins et al., "Advanced Detectors for Chemical Weapon Detection," $2^{nd}$ Joint Conf. Point Detection for Chem. and Bio. Defense, Mar. 1–5, 2004, which are incorporated herein by reference.

The mass-sensitive chemical preconcentrator combines an acoustic microbalance with the microhotplate of prior fixed-collection-time preconcentrators to actively measure the mass of the sample as it is collected and then rapidly heat and release the collected sample for further analysis. The mass-sensitive chemical preconcentrator can comprise any of the acoustic microbalances described herein. A preferred embodiment uses the PPR as the acoustic microbalance, since this resonator has very low heat capacity, good thermal stability, and a thin-film heater can be easily included in the fabrication process.

SAW devices rely on the electrical excitation of a surface acoustic wave in a piezoelectric substrate. Typically, a wave is established on a quartz surface and the collection of sample mass on the surface is reflected in the propagation of the surface wave. The high quality factor, Q, and low insertion loss of SAW chemical sensors makes them extremely stable in an oscillator circuit, resulting in low detection limits. SAW microbalances can detect sub nanogram-levels of chemical analytes. When used as a mass-sensitive chemical preconcentrator, the piezoelectric substrate can further comprise a resistive heating element disposed on the surface for heating of the collected sample. However, the SAW microbalance typically has a high thermal mass and is not ideal for rapid heating. Furthermore, SAW microbalances typically operate at hundreds of megahertz frequencies, complicating the design and integration of oscillator circuitry.

A resonant microbalance comprises a vibrating element, or resonator, of a certain shape. Depending on the shape, the resonator can support several types of vibrations, e.g., longitudinal, transverse, torsional, and lateral, that can have a number of vibrational modes or resonances. The stress, mass, or shape of the resonator is typically designed such that one of these modes dominates and the resonant frequency of the dominant mode is matched to a driving excitation signal. When used as a chemical sensor, the collection of sample mass on the surface of the resonator is measured as a change in the resonant frequency or the amplitude of the vibration. Resonators that operate on magnetic actuation principles are particularly attractive for chemical sensing, due to their large dynamic range and high sensitivity. Electromagnetic resonators rely on a Lorentz force, generated by an alternating electrical current flowing in the resonator interacting with an external magnetic field, to excite a mechanical vibration in the structure.

A magnetically excited FPW (mag-FPW) resonator is described in S. J. Martin et al., "Flexural plate wave resonator excited with Lorentz forces," *J. Appl. Phys.* 83(9), 4589 (1998) and U.S. Pat. No. 5,836,203, which are incorporated herein by reference. As shown in FIG. 1, the mag-FPW resonator typically comprises a meandering current conductor line 15 patterned on a silicon nitride membrane 13 that is suspended on a silicon frame 12. A Lorentz force is created by the interaction of an alternating surface current I flowing in the current conductor line 15 and an in-plane static magnetic field B perpendicular to the current flow direction. Preferential coupling to a particular membrane mode is achieved by positioning the current conductor line 15 along antinodes of the longitudinal mode. When the alternating current I has the natural frequency of the mag-FPW resonator, a large amplitude standing wave is set up in the membrane wave plate 13. The motion of the current conductor line 15 in the magnetic field B in turn induces a back electromotive force (back-emf) opposing the motion. This back-emf can be detected as an increase in impedance of the current conductor line 15. Alternatively, in a two-port mag-FPW resonator, the flexural plate wave motion of the membrane 13 driven by the first current conductor line 15 can be detected as an output voltage in a second current conductor line 19. When used as a mass-sensitive chemical preconcentrator 10, the mag-FPW resonator can further comprise a chemically sensitive coating 16 and a resistive heating element 18 on the membrane 13. The chemically sensitive coating 16 can sorb chemical species from the environment and the resistive heating element 18 can rapidly heat and desorb the collected sample.

Because the confinement of kinetic energy is in a thin, low-mass membrane, the FPW microbalance can have a very high mass sensitivity. Also, because the wave velocity in the FPW membrane is much less than in a solid substrate, the operating frequency of a FPW resonator is much lower than in a SAW device, resulting in simpler oscillator electronics. In addition, FPW resonators can be made with micromachining processes in a silicon wafer and can be integrated with microelectronic circuits. However, the temperature-dependent tension variation in the membrane, due to the differential thermal expansion of the silicon nitride membrane relative to the silicon frame, make the FPW operation very sensitive to temperature drift.

The mass-sensitive chemical preconcentrator preferably comprises a microfabricated PPR as the microbalance. The PPR is basically a small plate, or paddle, that pivots about two torsional pivot arms. As mass collects on a chemically selective coating on the paddle, or on the paddle itself, the resonant frequency of the PPR decreases, thereby providing a microbalance. The PPR provides a Q-factor, operating frequency, and mass sensitivity comparable to the FPW resonators, but with much better temperature stability. In particular, the PPR is about three orders of magnitude less sensitive to temperature drift than the FPW resonator, primarily because silicon is used as the paddle material, rather than silicon nitride. When used as a mass-sensitive chemical preconcentrator, thin-film heaters can be included in the fabrication of the PPR to provide a low heat capacity, thermally stable platform for sensitive, mass-activated release of a collected sample.

Figure 2:
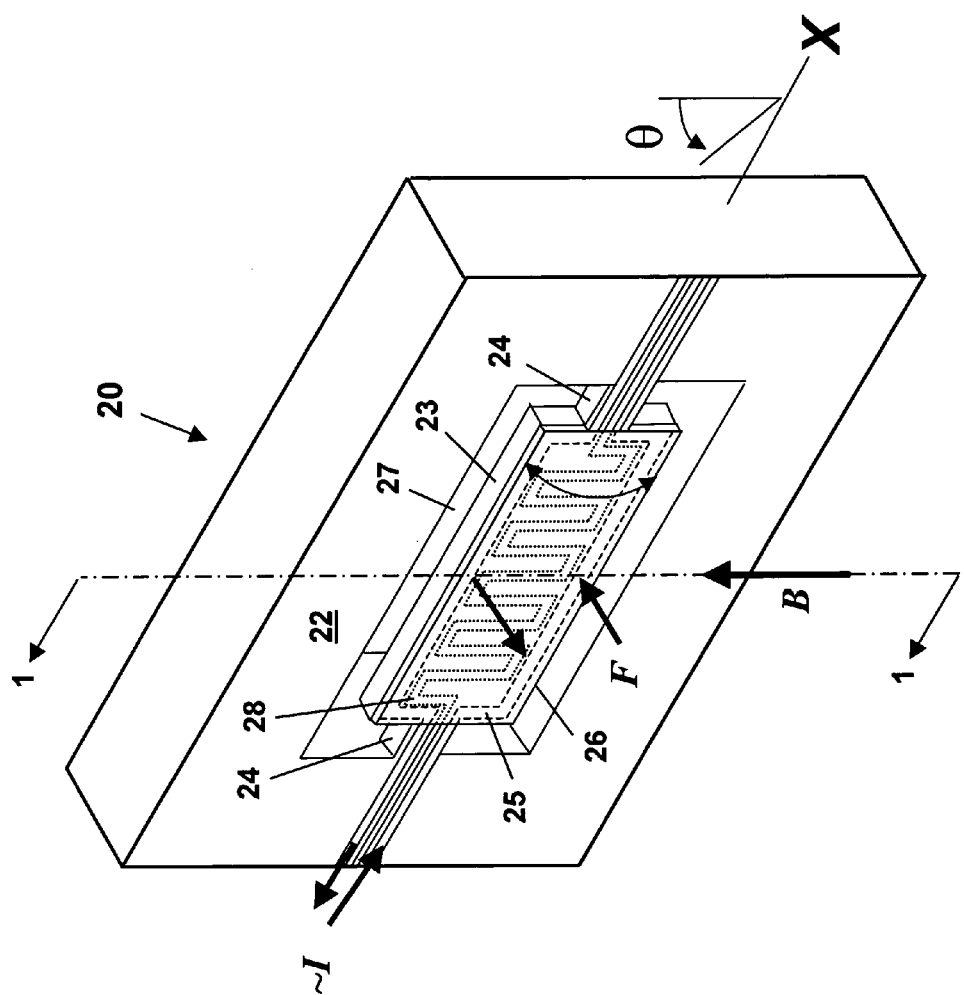
FIG. 2 shows a schematic illustration of a microfabricated mass-sensitive chemical preconcentrator that uses a pivot plate resonator (PPR) to actively measure the mass of a sample while it is being collected.

In FIG. 2 is shown a schematic illustration of a microfabricated PPR-based mass-sensitive chemical preconcentrator 20 that relies on the Lorentz force to excite a torsional oscillation in a paddle. The PPR comprises a frame 22, a paddle 23, torsional pivot arms 24, a current conductor line 25, means for applying a static magnetic field B in the plane of the paddle 23, and means for energizing the current conductor line 25 with an alternating electrical current I. The frame 22 is preferably a non-magnetic structural material, which typically can be silicon. Alternatively, other structural materials can be used. The paddle 23 is preferably a non-magnetic, semiconducting or insulating thin plate, which typically can be silicon, polysilicon, silicon nitride, silicon dioxide, or a polymer. When used as a chemical preconcentrator 20, the paddle 23 is preferably silicon to provide thermal stability of the resonant frequency of the PPR. Alternatively, the paddle 23 can be a conducting material with a thin insulating film (not shown) on the surface to provide electrical isolation of the current conductor line 25. The paddle 23 is preferably rectangular in shape, although other shapes can also be used. The pivot arms 24 pivotably anchor the oscillating paddle 23 to the stationary frame 22. The pivot arms 24 therefore define an axis of rotation X in the plane of the paddle 23. The rotational axis X is preferably the longitudinal axis of a rectangular paddle. A clearance gap 27 is provided to allow free oscillation of the paddle 23 within a cavity of the stationary frame 22 about the rotational axis X. The current conductor line 25 is displaced from the rotational axis X of the paddle 23. Preferably, the conductor line 25 runs around the periphery of the paddle 23 to provide a large Lorentz force F.

The mass-sensitive chemical preconcentrator 20 further comprises a resistive heating element 28 disposed on a surface of the paddle 23. The resistive heating element 28 can comprise a resistive conducting material. The resistive heating element 28 can be formed by depositing one or more layers of a metal or metal alloy over the paddle 23 and patterning the layers to form the desired heater shape. Alternatively, the resistive heating element 28 can be a doped semiconductor material, such as doped silicon. Preferably, the patterned metal layer comprises a circuitous or serpentine shape that uniformly heats the paddle 23. Preferably, the resistive layer has a suitably high temperature of coefficient of resistance (TCR of 2500–3000 ppm/°C.) to facilitate temperature measurement and control. Alternatively, a separate temperature sensor (not shown) can be used to control and measure the temperature during heating of the paddle 23. The resistive heating element 28 can further include a plurality of bond pads (not shown) for electrical contact to a power source. The resistive heating element 28 can be heated directly by an electrical current or inductively.

The mass-sensitive chemical preconcentrator 20 can further comprise a chemically sensitive coating 26 disposed on one or both surfaces of the paddle 23 to sorb chemical species from the environment. The chemically sensitive coating 26 can be a chromatographic stationary phase, polymer, getter, sol-gel, or other sorbent material. The coating 26 can be chosen to be sensitive to or have a high affinity for the analyte that one desires to detect. In addition, the coating 26 should preferably provide a rapid, reversible, and reproducible response to the sorbed analyte, stable chemical and physical properties, good adhesion to the paddle 23, and consistent coating behavior. Once the desired amount of sample has been collected, the sorbed sample can be rapidly released upon heating of the sorptive material 26 by the resistive heating element 28.

The source of the magnetic field B can be a conventional permanent magnet, direct-current (DC) coils, or the like. The magnetic field B is aligned substantially parallel to the plane of the paddle 23 and substantially perpendicular to the current direction in the conductor line 25 and the axis of rotation X. As shown in FIG. 2, application of an electrical current I to the conductor line 25 generates a surface-normal Lorentz force F directed according to the right-hand rule. The torque resulting from the Lorentz force F is resisted by the torsional spring restoring force resulting from the twisting of the pivot arms 24. Furthermore, because of the static B field, an alternating electrical current I through the conductor line 25 generates a reversing direction of the Lorentz force F on the paddle 23, causing the paddle 23 to oscillate from its rest position about the axis of rotation X.

At a certain frequency, a resonant mode is established and the paddle 23 undergoes maximum oscillations. The resonant frequency can be determined from the differential equation-of-motion for a pivot plate resonator:

$$J\ddot{\theta} + C_t\dot{\theta} + k\theta = T \quad (1)$$

where $\theta$ is the torsional angle of the paddle oscillation about the axis of rotation X, J is the polar moment of inertia of the paddle cross-section about the rotational axis X, $C_t$ is the damping coefficient due to structural damping and viscous dissipation due to fluid loading, and T is the time-dependent applied torque.

Figure 3:
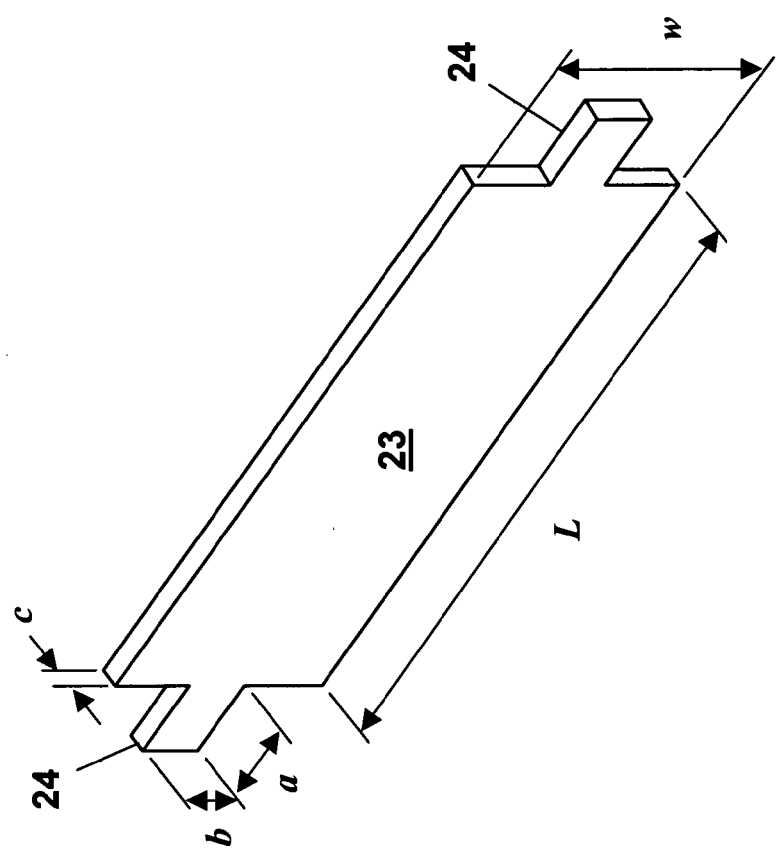
FIG. 3 shows a schematic illustration of a rectangular paddle of the PPR.

Shown in FIG. 3 is a schematic illustration of a rectangular paddle 23. The rectangular paddle 23 has a width w, length L, thickness c, and effective density $\rho$. The pivot arms 24 have a length a and width b. Therefore, the polar moment of inertia of the rectangular cross-section is $J=\rho wcL(c^2+w^2)/12$. For a current conductor line 25 running around the perimeter of the rectangular paddle 23, the applied torque is T=Fw=BILw, where B is the static magnetic flux, and I is the time-varying current through the conductor line 25. The torsional spring constant of the pivot arms 24 is $$k = 2\beta bc^3 G/a \quad (2)$$

where G is the shear modulus of elasticity of the pivot arm material. $\beta$ is a parameter that depends on the ratio b/c of the long side to the short side of the rectangular cross-section of the pivot arm 24 that is twisted. For a thin section (b>>c), $\beta$ is approximately ⅓.

The steady-state solution to the equation-of-motion, eq. (1), has the form $$\theta = \bar{\Theta}\exp(j\omega t) = |\bar{\Theta}|\exp j(\omega t - \phi_d) \quad (3)$$

where the amplitude is $$|\bar{\Theta}| = \frac{BwLI/k}{\sqrt{(1-r^2)^2 + (2\zeta r)^2}} \quad (4)$$

and where $r=\omega/\omega_n$, and $\zeta=C_t/2\sqrt{kJ}=\frac{1}{2}Q$. Q is the mechanical quality factor of the resonator. The phase of the rotational displacement relative to the drive current is $$\phi_d = \tan^{-1}\frac{2\zeta r}{1-r^2} \quad (5)$$

The natural resonant frequency of oscillation is $$\omega_n = \sqrt{k/J} \quad (6)$$

Therefore, changing the cross section or length of the pivot arms 24 or the dimensions or mass of the paddle 23 will alter the resonant frequency $\omega_n$ and the phase shift of the oscillations at resonance. In particular, for the mass-sensitive chemical preconcentrator of the present invention, both the resonant frequency $\omega_n$ and phase $\phi_d$ are changed, through the dependence of the moment of inertia J on the absorbed mass, when a chemical sample is absorbed or desorbed from the chemically sensitive coating 26 or the paddle 23.

Importantly for chemical sensing, the PPR is relatively insensitive to temperature drift, since the shear modulus of elasticity G, which determines the torsional spring constant k, has only a small variation with temperature. However, for some applications, the temperature dependence of the shear modulus can be exploited to vary the resonant frequency of the PPR. Tests have shown that the resonant frequency decreases about 1 Hz for each 1° F. increase in temperature. Therefore, the resonant frequency can be altered and actively controlled by heating the paddle and pivot arms.

The motion of the current conductor line 25 in the magnetic field B induces a back-emf in the conductor line 25 opposing the motion. The back-emf is $$E = BwL\frac{d\theta}{dt} \quad (7)$$

and it is electrically manifested as a change in the impedance (i.e., "motional resistance") of the current conductor line 25. The amplitude of the resonator impedance is $$Z = \frac{V}{I} = Z_0 + Z_D = Z_0 - \frac{BwLj\omega\Theta}{I} = |Z|\exp(j\phi_z) \quad (8)$$

where $Z_0$ is the DC resistance of the resonator, $Z_D$ is the impedance change due to the back-emf, and $$|Z| = \quad (9)$$

$$\frac{(BwL)^2 r}{J\omega_n}\sqrt{\left(\frac{Z_0 J\omega_n}{(BwL)^2 r} + \frac{2r\zeta}{(1-r^2)^2 + (2r\zeta)^2}\right)^2 + \left(\frac{(1-r^2)}{(1-r^2)^2 + (2r\zeta)^2}\right)^2}$$

and $$\phi_z = \arctan\left(\frac{(1-r^2)}{\frac{Z_0 J\omega_n}{(BwL)^2 r}[(1-r^2)^2 + (2r\zeta)^2] + 2r\zeta}\right) \quad (10)$$

The impedance change $Z_D$ can be used to sense the pivot plate resonances. In a one-port device, the excitation and detection of the oscillation of the PPR and its resonant frequency $\omega_n$ can be obtained directly through the ratio of the drive voltage to the drive current (i.e., an impedance response). Alternatively, in a two-port device, a second conductor line (not shown) can be run in a different region of the paddle 23 (e.g., on the back side of the paddle 23) and the oscillation excited by the first current conductor line 25 can be sensed as an output voltage induced in the second current conductor line.

Figure 4:
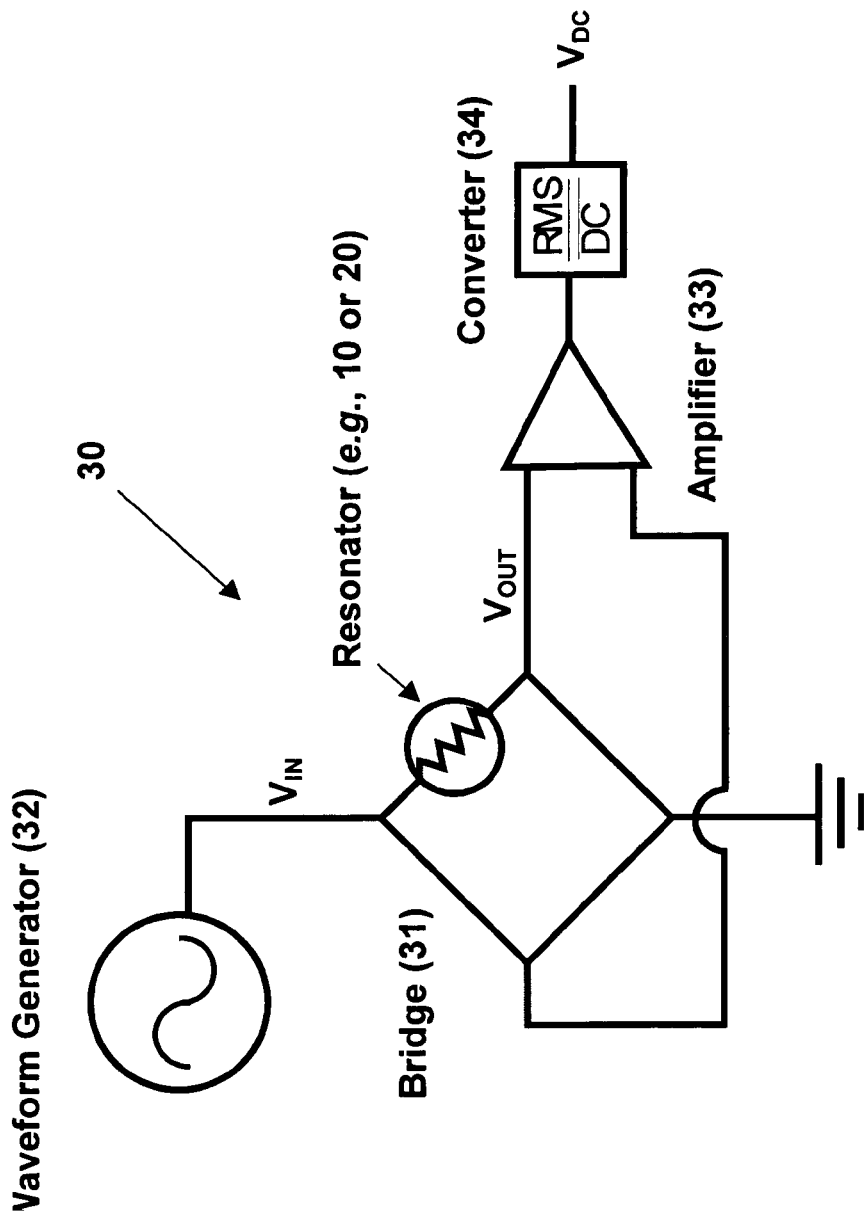
FIG. 4 shows a simple drive and sense circuitry with the PPR forming the active leg of a Wheatstone bridge.

The impedance response of the PPR can be measured with an electronic oscillator circuit and a bridge circuit. In FIG. 4 is shown a simple excitation and detection circuit 30 that can be used to drive the resonator and sense the impedance change $Z_D$ due to the back-emf. The simple circuit 30 comprises a Wheatstone bridge circuit 31, a waveform generator 32 to drive the bridge 31 with a sinusoidal supply voltage $V_{IN}$, an operational amplifier 33 to amplify the bridge voltage $V_{OUT}$, and an RMS-to-DC converter 34 to convert the amplifier output to a DC output voltage $V_{DC}$. A single resonator forms the active leg of the bridge circuit 31. Therefore, the bridge output voltage is proportional to the relative change of the resonator's impedance according to $$V_{OUT} = \left(\frac{1}{2} - \frac{Z_0}{2Z_0 + Z_D}\right) V_{IN} \quad (11)$$

where $Z_0$ is the ohmic resistance of the current conductor line 25 and $Z_D$ is the impedance change resulting from the back-emf. When the resonator is not operating at resonance, the bridge 31 is balanced and the differential output $V_{OUT}$ from the bridge 31 is zero. At resonance, the resonator's impedance increases, due to the back-emf, and the bridge 31 is unbalanced, resulting in an AC bridge voltage $V_{OUT}$ at the input of the amplifier 33. This AC bridge voltage $V_{OUT}$ can be amplified and converted to a DC output voltage $V_{DC}$ by the RMS-to-DC converter 34.

The mass-sensitive chemical preconcentrator can be fabricated by micromachining techniques generally known to the integrated circuits manufacturing industry. Such methods enable batch fabrication and monolithic integration of the preconcentrator with on-chip electronic circuitry.

In FIGS. 5a–5j are shown cross-sectional views, along the lines 1—1 in FIG. 2, of a method to fabricate the PPR-based mass-sensitive chemical preconcentrator 20, starting with a silicon-on-insulator (SOI) substrate having a top silicon layer separated from a silicon substrate by an intermediate buried SiO$_2$ layer. The SOI method comprises the steps of depositing the current conductor line 25, resistive heating element 28, and bond pads on the top silicon layer; patterning the top silicon layer to define the paddle 23, the pivot arms 24, and the inner wall of the frame 22; forming a cavity in the backside of the silicon substrate, underneath the paddle, pivot arms, and clearance gap regions, to provide the frame 22; and releasing the paddle 23 from the frame 22 by removing the clearance gap portion of the buried oxide layer. A chemically sensitive coating 26 can be formed on at least one surface of the paddle 23.

Figure 5A:
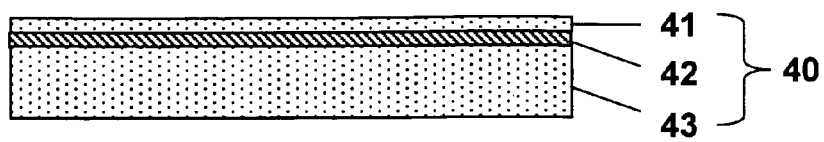
FIGS. 5a–5j show schematic cross-section views, along the lines 1—1 in FIG. 2, of a method to fabricate a PPR-based mass-sensitive chemical preconcentrator.

In FIG. 5a is shown a cross section of a commercially available SOI substrate 40 comprising a top silicon layer 41 (e.g., 1- to 10-μm thickness) separated from a silicon substrate 43 (e.g., 400- to 500-μm thickness) by a buried oxide layer 42 (e.g., about 1 μm thickness). The SOI substrate 40 can be formed, for example, by a wafer bonding and etch-back method wherein a silicon wafer is thermally bonded to another silicon wafer by a thermally grown silicon dioxide intermediate layer. One of the silicon wafers is subsequently polished or etched down to the desired thickness to provide the top silicon layer 41. The top silicon layer 41 can therefore be single crystal silicon having good, consistent mechanical properties. The top silicon layer 41 can be undoped or lightly doped to provide low electrical conductivity. Alternatively, the top silicon layer 41 can be coated with a thin insulating layer (e.g., less than 50 nm of silicon nitride or silicon dioxide, not shown) to provide electrical isolation of the current conductor line 25. The buried oxide 42 provides a highly selective etch stop layer for subsequent etching of the top silicon layer 41 and the silicon substrate 43.

Figure 5B:
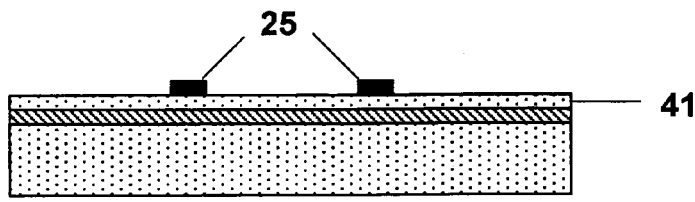

In FIG. 5b, a frontside metallization layer can be deposited and patterned on the top silicon layer 41 to provide the current conductor line 25. The frontside metallization layer can be patterned by a liftoff or an etch process, depending on the metal used. The metallization can comprise a high-conductivity metal, such as gold, aluminum, or platinum, having sufficient cross section to provide a current conductor line 25 having high electrical conductivity. The metal should also be compatible with subsequent processing. For example, the current conductor line 25 can be a gold line having a width of 40 μm and a thickness of 500 nanometers that can run around the periphery of the paddle 23.

Figure 5C:
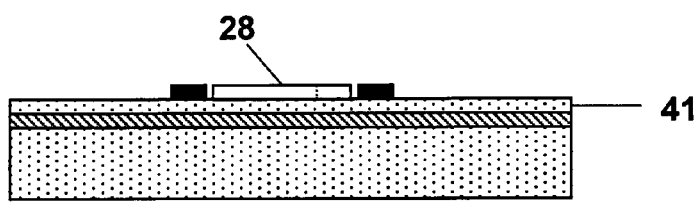

In FIG. 5c, a frontside metallization layer can be deposited and patterned on the top silicon layer 41 to provide the resistive heating element 28. The frontside metallization layer can be patterned by a liftoff or an etch process, depending on the metal, used to form the desired heater shape. The resistive heating element 28 can comprise a resistive conducting material, such as a metal or metal alloy. The metallization layer can include an adhesion layer (e.g., chromium) and a resistive layer (e.g., platinum, palladium, chromium, titanium, molybdenum, tungsten, or combinations thereof). Alternatively, the resistive heating element 28 can be a doped semiconductor material, such as doped silicon. Preferably, the patterned metal layer comprises a circuitous or serpentine shape to uniformly heat the paddle 23. Other arrangements of resistive heating elements, that substantially cover the area of the paddle and are thermally isolated from the substrate by their placement on the paddle, are possible. Preferably, the resistive layer has a suitably high temperature of coefficient of resistance (TCR of 2500–3000 ppm/°C.) to facilitate temperature measurement and control. Alternatively, a separate temperature sensor (not shown) can be used to control and measure the temperature during heating of the sorption support structure. The resistive heating element 28 can further include a plurality of bond pads (not shown) for electrical contact to a power source. The metallization should also be compatible with subsequent processing.

Alternatively, the same front metallization layer can be patterned to form both the current conductor line 25 and the resistive heating element 28 in a single step. For example, the resistive heating element 28 can be a gold line having a width of 10 μm and a thickness of 500 nanometers on a chromium adhesion layer of 0.5 nanometers thickness on the paddle 23.

Figure 5D:
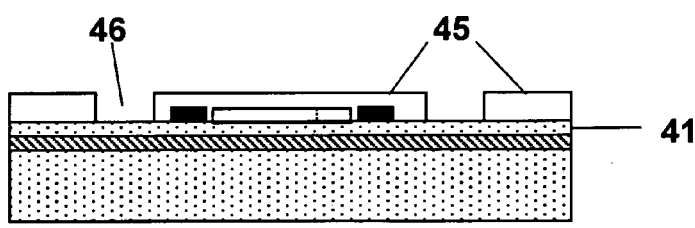

In FIG. 5d, a frontside photoresist layer 45 can be spun-on the front surface of the top silicon layer 41. The frontside photoresist layer 45 can be lithographically exposed and developed to provide openings 46 to define the paddle 23 and pivot arms 24 and the inner wall of the frame 22.

Figure 5E:
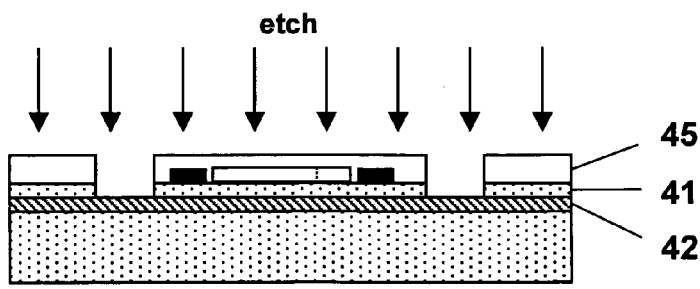

In FIG. 5e, the top silicon layer 41 can be patterned by etching through the openings 46 in the developed frontside photoresist layer 45 to provide the silicon portion of the paddle 23 and pivot arms 24. The exposed silicon can be removed by deep reactive ion etching (DRIE) using fluorine-based etchants (e.g., SF$_6$, C$_4$F$_8$). The DRIE etch will stop at the highly selective buried oxide layer 42 and provide well-defined, steep sidewalls in the patterned top silicon layer 41.

Figure 5F:
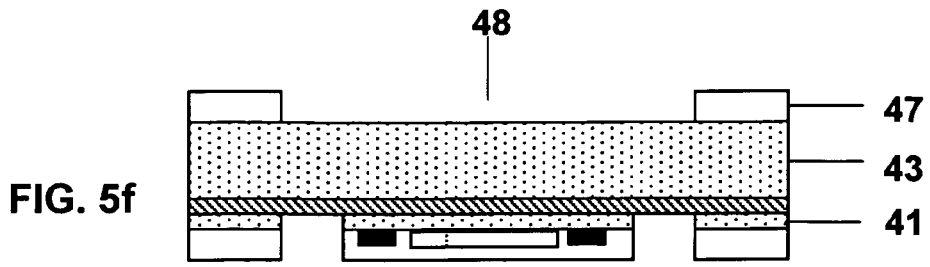

In FIG. 5f, the SOI substrate 40 can be flipped over and a backside photoresist layer 47 can be applied to the back surface of the silicon substrate 43. The photoresist layer 47 can be lithographically exposed and developed to provide an opening 48 to subsequently form a cavity in the silicon substrate 43 underneath the portion of the top silicon layer 41 that forms the paddle 23, pivot arms 24, and clearance gap 27.

Figure 5G:
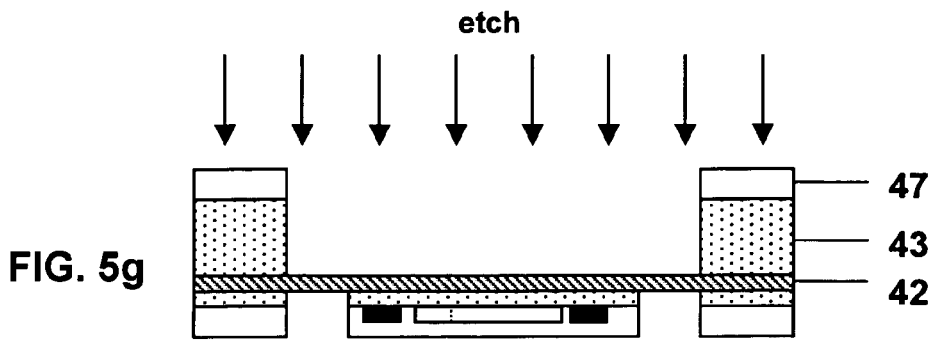

In FIG. 5g, the silicon substrate 43 can be etched through the opening 48 in the developed backside photoresist layer 47 by DRIE to form the cavity in the silicon substrate 43.

The DRIE etch will effectively stop when it reaches the backside of the buried oxide 42.

Figure 5H:
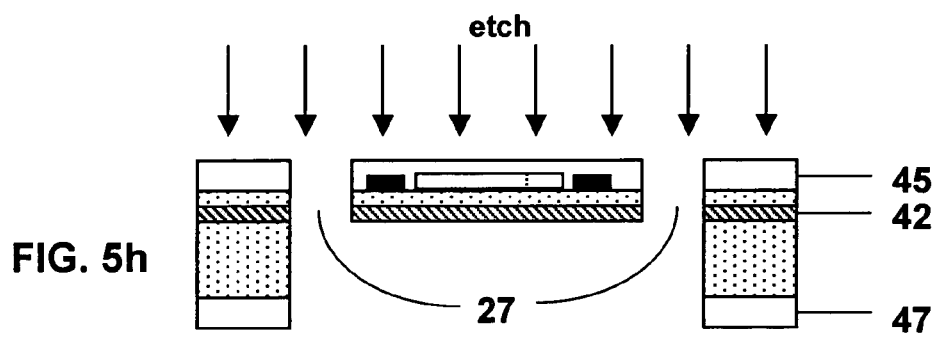

In FIG. 5h, the SOI substrate 40 can be flipped over and the frontside of the buried oxide layer 42 can be etched through the openings 46 in the developed frontside photoresist layer 45. The exposed silicon dioxide can be removed using a plasma-based etching process with fluorine-based etchants (e.g., CHF, $C_2F_6$) to complete the clearance gap 27 and release the structure. The clearance gap 27 allows the paddle 23 to freely oscillate within the cavity of the frame 22.

Figure 5I:
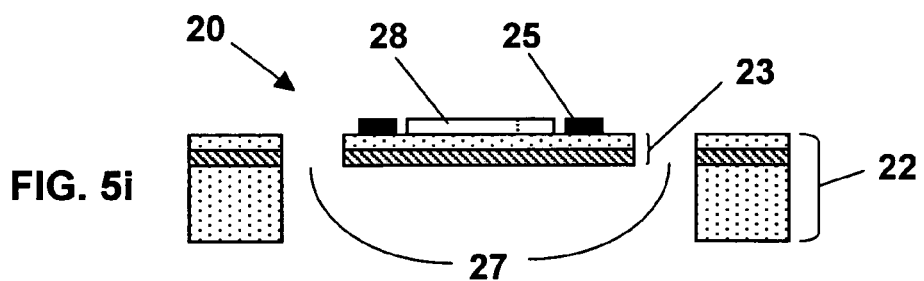

In FIG. 5i, the frontside and backside photoresist layers 45 and 47 can be stripped by standard solvents to provide the mass-sensitive chemical preconcentrator 20, comprising the frame 22, paddle 23, pivot arms 24 (not shown in this cross-sectional view), current conductor line 25, and resistive heating element 28.

Figure 5J:
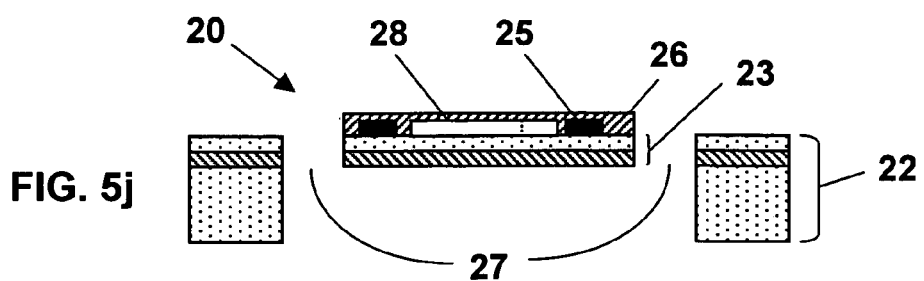

In FIG. 5j, a chemically sensitive coating 26 can be formed on one (as shown) or both surfaces of the paddle 23 to enhance sorption of a gas or vapor of interest thereon. The chemically sensitive coating 26 can be a chromatographic stationary phase, polymer, getter, sol-gel, or other sorbent material. Several of these polymer coatings, such as polyisobutylene, substituted polysiloxanes, and ethyl cellulose, have been developed for quartz crystal microbalances, SAW sensors, and FPW sensors. See J. W. Grate, "Acoustic Wave Microsensor Arrays for Vapor Sensing," *Chem. Rev.* 2000, 100, 2627–2648, which is incorporated herein by reference. Depending on the sorbent material, the coating 26 can be applied by solvent casting, spraying, vapor deposition, electrochemical deposition, photo-polymerization, plasma polymerization, self-assembling deposition, photopatterning, or the like. The coating 26 can be chosen to be sensitive to or have a high affinity for the analyte that one desires to detect. In addition, the coating 26 should preferably provide a rapid, reversible, and reproducible response to the sorbed analyte, stable chemical and physical properties, good adhesion to the paddle 23, and consistent coating behavior. Alternatively, the paddle material itself may sorb the analyte without the need for a coating 26.

To improve collection in a sample stream containing multiple analytes, an array of mass-sensitive chemical preconcentrators, each having a different partially selective coating, can be used. The response of each preconcentrator is thereby related to the different interactions between the analytes and the selective coatings. Therefore, such a preconcentrator array can provide sensitivity over a wider range of analytes, improved selectivity, and simultaneous multicomponent analysis. In particular, the resonator array may be able to collect individual analytes in a mixture, if a sufficiently diverse set of selective coatings is used. For portable applications, the area occupied by the microfabricated preconcentrators can be relatively small and they can be integrated with on-board electronics to reduce the size and cost of the analytical instrument.

The resonator of the PPR-based chemical preconcentrator is sensitive to mass loading on the paddle surface. The mass change due to the sorbed sample can be actively measured gravimetrically as a proportional change in the resonator's response during the collection process. The resonant frequency is inversely related to the moment of inertia of the paddle and the combined mass of the paddle, coating, and absorbed sample. Therefore, the mass of the collected sample in a fluid stream can be determined by measuring the change in resonant frequency $\omega_n$ or phase $\phi_d$ of the resonator as the sample is absorbed onto the paddle. A sensitivity of 9 degrees of phase shift per nanogram of dimethyl methyl phosphonate (DMMP) has been demonstrated on a PPR not optimized for mass collection. Accurate theoretical models of the PPR-based chemical preconcentrator performance indicates that sensitivity of 0.1 nanogram or better can be obtained. Following sample collection, the paddle can be rapidly heated to release the sample for further analysis. The preconcentrator can reach a desorption temperature of 200° C. in 24 milliseconds with only 100–150 mW of power, depending mainly on the thickness of the silicon paddle layer (i.e., 2 to 5 microns, respectively). The resonant frequency of the PPR is not altered by desorption heating cycles. Therefore, the PPR-based mass-sensitive chemical preconcentrator can be used repeatedly to optimize the sample collection time and enable the rapid and accurate analysis of analytes by the microanalytical system.

Figure 6B:
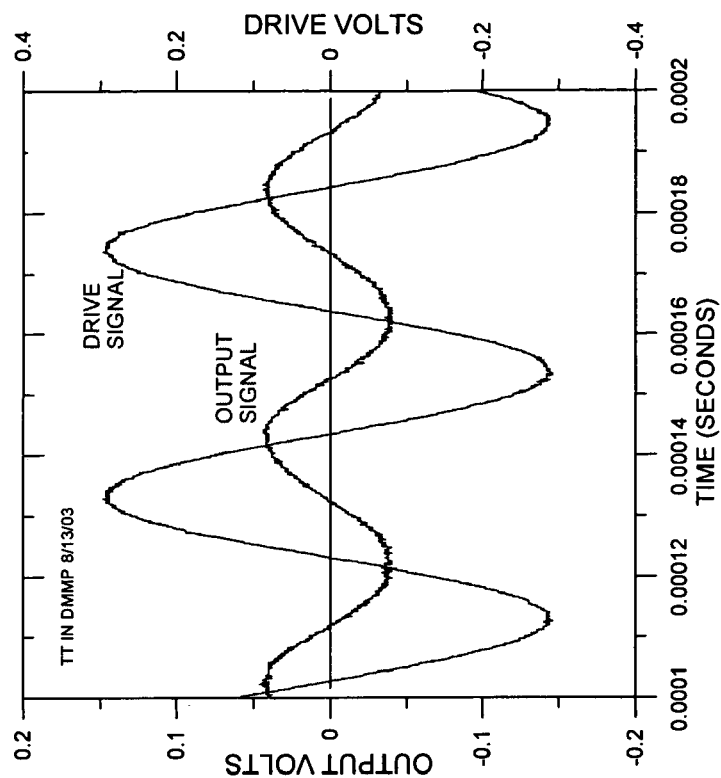
FIGS. 6a and 6b show the drive and output signals for a PPR-based mass-sensitive chemical preconcentrator with and without analyte present in the sample stream, respectively.
Figure 6A:
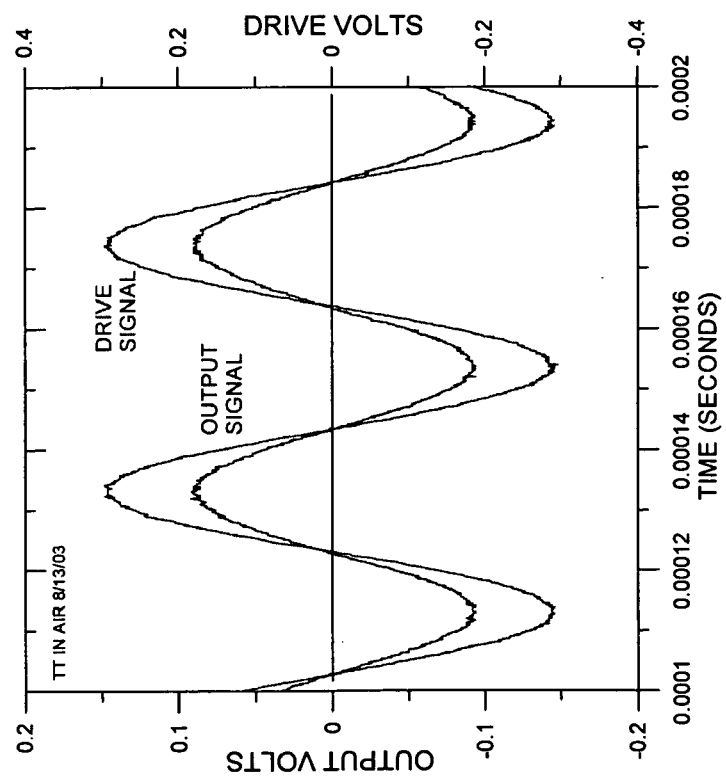

In FIGS. 6a and 6b are shown the drive and output signals for a PPR-based mass-sensitive chemical preconcentrator, with and without analyte present in the sample stream, respectively. FIG. 6a shows the drive and output signals when the paddle was coated with a sol-gel adsorbent coating, but with no sorbed analyte. FIG. 6b shows the drive and output signals for the same preconcentrator after 10 nanograms of DMMP was collected by the sol-gel coating on the paddle. Both the phase and amplitude of the output signal changed after the DMMP was collected. In particular, the 10 nanograms collected provided about 90° of phase shift.

Figure 7:
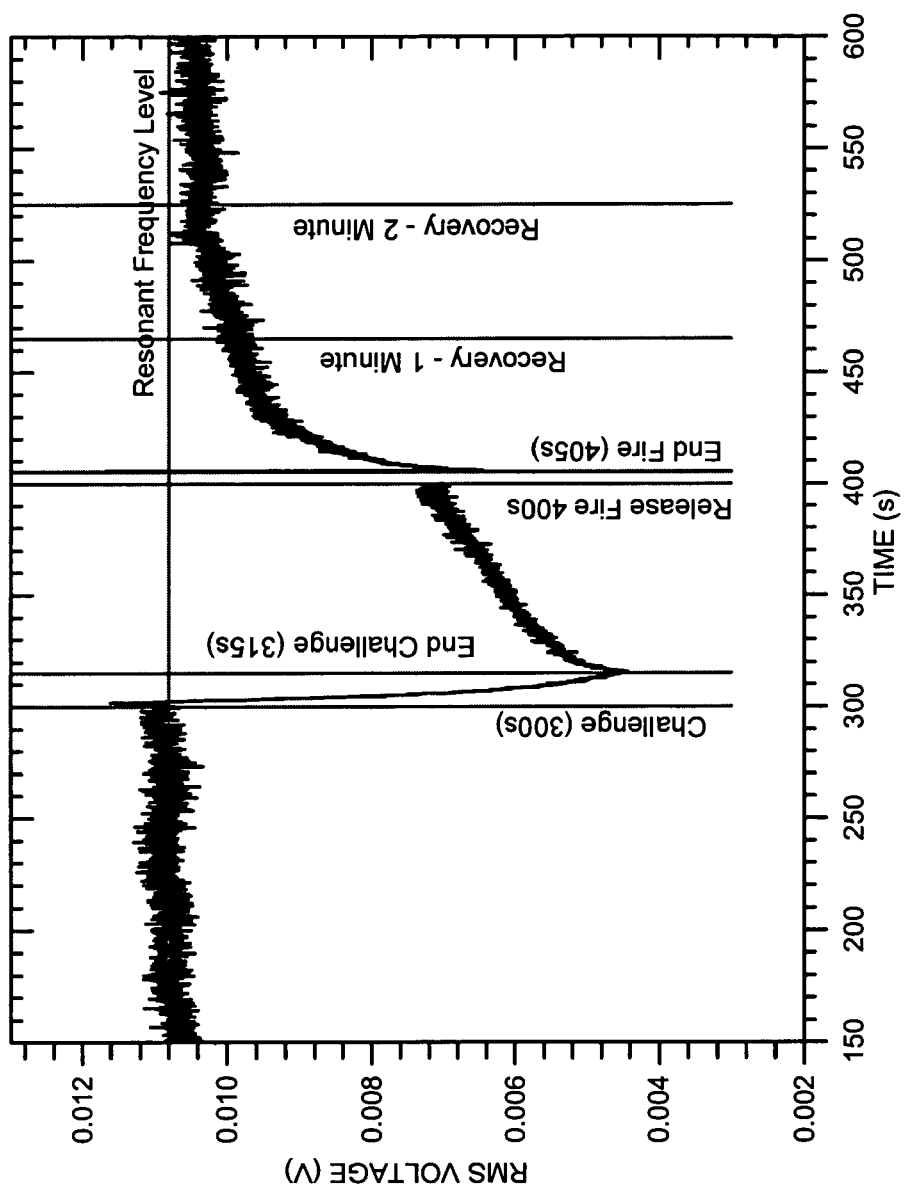
FIG. 7 shows the collection and desorption of dimethyl methyl phosphonate (DMMP) from a PPR-based mass-sensitive chemical preconcentrator.

FIG. 7 shows the collection and desorption of DMMP from the PPR-based mass-sensitive chemical preconcentrator, as sensed by the change in the RMS voltage of the output signal as a function of time. After a baseline response was established, 1200 ppm of DMMP was introduced into the preconcentrator for 15 seconds. The preconcentrator is capable of holding onto some of the analyte, as seen from the slow increase in the output signal 315 to 400 seconds. At 400 seconds, a 5 second, 200° C. heating pulse was applied, releasing the analyte. The analyte was released within a few tenths of a second. The PPR cooled after application of the heating pulse and returned to baseline in about 120 seconds.

The present invention has been described as a mass-sensitive chemical preconcentrator. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A mass-sensitive chemical preconcentrator for collecting and releasing a chemical sample, comprising:
   a pivot plate resonator, comprising
      a frame,
      a paddle having a first surface and a second surface for collection of the sample thereon, the paddle further having a first end and a second end, wherein the paddle is pivotably anchored to the frame by pivot arms at each end of the paddle and wherein the pivot arms define an axis of rotation of the paddle,
      a current conductor line disposed on a surface of the paddle that is displaced from the axis of rotation of the paddle,
      means for applying a static magnetic field aligned substantially in-plane with the paddle and substantially perpendicular to the current conductor line and the axis of rotation, and
      means for energizing the current conductor line with an alternating electrical current to excite an oscillatory motion of the paddle about the axis of rotation;

a resistive heating element disposed on a surface of the paddle; and means for energizing the resistive heating element to thermally release the collected sample from the paddle.

2. The chemical preconcentrator of claim 1, further comprising a means for detecting the oscillatory motion of the paddle.

3. The chemical preconcentrator of claim 2, wherein the detecting means comprises measuring the impedance of the current conductor line.

4. The chemical preconcentrator of claim 2, wherein the detecting means comprises measuring the phase of the current relative to the voltage of the current conductor line.

5. The chemical preconcentrator of claim 2, wherein the detecting means comprises measuring the phase of the current relative to the rotational displacement of the oscillatory motion.

6. The chemical preconcentrator of claim 1, further comprising a second current conductor line on a surface of the paddle that is displaced from the axis of rotation of the paddle for detection of the oscillatory motion excited by the energizing of the current conductor line with the alternating electrical current.

7. The chemical preconcentrator of claim 6, further comprising a means for measuring the output voltage induced in the second current conductor line.

8. The chemical preconcentrator of claim 1, wherein the current conductor line substantially follows the periphery of the paddle.

9. The chemical preconcentrator of claim 1, wherein the paddle comprises a rectangular shape.

10. The chemical preconcentrator of claim 1, wherein the frame comprises silicon.

11. The chemical preconcentrator of claim 1, wherein the paddle comprises silicon, polysilicon, silicon nitride, silicon dioxide, or polymer.

12. The chemical preconcentrator of claim 1, further comprising an insulating thin film on a surface of the paddle to provide electrical isolation of the current conductor line.

13. The chemical preconcentrator of claim 1, wherein the means for energizing the current conductor line with the alternating electrical current excites the oscillatory motion of the paddle in a resonant mode.

14. The chemical preconcentrator of claim 1, further comprising a chemically sensitive coating disposed on at least one surface of the paddle.

15. The chemical preconcentrator of claim 14, wherein the chemically sensitive coating comprises a chromatographic stationary phase, getter, sol-gel, or polymer.

16. The chemical preconcentrator of claim 1, wherein the resistive heating element comprises a circuitous metal trace.

17. The chemical preconcentrator of claim 16, wherein the metal comprises a metal selected from the group consisting of gold, aluminum, platinum, molybdenum, titanium, chromium, palladium, tungsten, and combinations thereof.

* * * * *